US008954146B2

(12) United States Patent
Hopper et al.

(10) Patent No.: US 8,954,146 B2
(45) Date of Patent: *Feb. 10, 2015

(54) IMPLANTABLE CARDIAC DEVICE WITH DYSPNEA MEASUREMENT

(71) Applicant: Cardiac Pacemakers, Inc., St. Paul, MN (US)

(72) Inventors: Donald L. Hopper, Maple Grove, MN (US); John Voegele, Bethel, MN (US); Jesse W. Hartley, Lake Elmo, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/254,464

(22) Filed: Apr. 16, 2014

(65) Prior Publication Data
US 2014/0221853 A1    Aug. 7, 2014

Related U.S. Application Data

(60) Continuation of application No. 13/967,864, filed on Aug. 15, 2013, now Pat. No. 8,750,992, which is a
(Continued)

(51) Int. Cl.
*A61N 1/00* (2006.01)
*A61B 5/00* (2006.01)
(Continued)

(52) U.S. Cl.
CPC .............. *A61B 5/686* (2013.01); *A61N 1/3627* (2013.01); *A61N 1/3702* (2013.01);
(Continued)

(58) Field of Classification Search
USPC ................... 600/484, 547; 607/17, 18, 19, 20
See application file for complete search history.

(56) References Cited

U.S. PATENT DOCUMENTS 4,312,734 A   1/1982   Nichols
4,365,636 A   12/1982  Barker
(Continued)

FOREIGN PATENT DOCUMENTS

EP        0750920        1/1997
EP        0770407        5/1997
(Continued)

OTHER PUBLICATIONS

"Aircraft Noise and Sleep Disturbance: Final Report," Civil Aviation Authority London on behalf of the Department of Trade (CAA Report), Aug. 1980.
(Continued)

*Primary Examiner* — Christopher D Koharski
*Assistant Examiner* — Roland Dinga
(74) *Attorney, Agent, or Firm* — Seager, Tufte & Wickhem, LLC

(57) ABSTRACT

Cardiac monitoring and/or stimulation methods and systems employing dyspnea measurement. An implantable cardiac device may sense transthoracic impedance and determine a patient activity level. An index indicative of pulmonary function is implantably computed to detect an episode of dyspnea based on a change, trend, and/or value exceeding a threshold at a determined patient activity level. Trending one or more pulmonary function index values may be done to determine a patient's pulmonary function index profile, which may be used to adapt a cardiac therapy. A physician may be automatically alerted in response to a pulmonary function index value and/or a trend of the patient's pulmonary index being beyond a threshold. Computed pulmonary function index values and their associated patient's activity levels may be stored periodically in a memory and/or transmitted to a patient-external device.

20 Claims, 7 Drawing Sheets

Related U.S. Application Data continuation of application No. 12/695,895, filed on Jan. 28, 2010, now Pat. No. 8,515,535, which is a division of application No. 11/067,964, filed on Feb. 28, 2005, now Pat. No. 7,680,534.

(51) Int. Cl.

| | |
|---|---|
| *A61N 1/362* | (2006.01) |
| *A61N 1/37* | (2006.01) |
| *A61N 1/365* | (2006.01) |
| *A61B 5/0205* | (2006.01) |
| *A61B 5/04* | (2006.01) |
| *A61B 5/0402* | (2006.01) |
| *A61B 5/11* | (2006.01) |
| *A61B 5/08* | (2006.01) |
| *A61B 5/091* | (2006.01) |

(52) U.S. Cl.
CPC ......... *A61N 1/36585* (2013.01); *A61B 5/0205* (2013.01); *A61B 5/04012* (2013.01); *A61B 5/0402* (2013.01); *A61B 5/1118* (2013.01); *A61B 5/4836* (2013.01); *A61B 5/746* (2013.01); *A61B 5/747* (2013.01); *A61B 5/0816* (2013.01); *A61B 5/091* (2013.01)
USPC ............................................................ 607/9

(56) References Cited

U.S. PATENT DOCUMENTS

| | | |
|---|---|---|
| 4,390,405 A | 6/1983 | Hahn et al. |
| 4,562,841 A | 1/1986 | Brockway et al. |
| 4,702,253 A | 10/1987 | Nappholz et al. |
| 4,777,962 A | 10/1988 | Watson et al. |
| 4,784,162 A | 11/1988 | Ricks et al. |
| 4,802,485 A | 2/1989 | Bowers et al. |
| 4,813,427 A | 3/1989 | Schlaefke et al. |
| 4,827,935 A | 5/1989 | Geddes et al. |
| 4,827,943 A | 5/1989 | Bornn et al. |
| 4,830,008 A | 5/1989 | Meer |
| 4,836,219 A | 6/1989 | Hobson et al. |
| 4,856,524 A | 8/1989 | Baker, Jr. |
| 4,875,477 A | 10/1989 | Waschke et al. |
| 4,928,688 A | 5/1990 | Mower |
| 4,953,551 A | 9/1990 | Mehra et al. |
| 4,958,632 A | 9/1990 | Duggan |
| 4,961,423 A | 10/1990 | Canducci |
| 4,972,842 A | 11/1990 | Korten et al. |
| 4,982,738 A | 1/1991 | Griebel |
| 5,010,888 A | 4/1991 | Jadvar et al. |
| 5,024,222 A | 6/1991 | Thacker |
| 5,036,849 A | 8/1991 | Hauck et al. |
| 5,047,930 A | 9/1991 | Martens et al. |
| 5,063,927 A | 11/1991 | Webb et al. |
| 5,105,354 A | 4/1992 | Nishimura |
| 5,123,425 A | 6/1992 | Shannon, Jr. et al. |
| 5,133,353 A | 7/1992 | Hauser |
| 5,146,918 A | 9/1992 | Kallok et al. |
| 5,156,157 A | 10/1992 | Valenta, Jr. et al. |
| 5,170,784 A | 12/1992 | Ramon et al. |
| 5,174,287 A | 12/1992 | Kallok et al. |
| 5,178,156 A | 1/1993 | Takishima et al. |
| 5,179,945 A | 1/1993 | Van Hofwegen et al. |
| 5,183,038 A | 2/1993 | Hoffman et al. |
| 5,187,657 A | 2/1993 | Forbes |
| 5,188,106 A | 2/1993 | Nappholz et al. |
| 5,199,424 A | 4/1993 | Sullivan et al. |
| 5,203,348 A | 4/1993 | Dahl et al. |
| 5,209,229 A | 5/1993 | Gilli |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,245,995 A | 9/1993 | Sullivan |
| 5,259,373 A | 11/1993 | Gruenke et al. |
| 5,261,400 A | 11/1993 | Bardy |
| 5,275,159 A | 1/1994 | Griebel |
| 5,280,791 A | 1/1994 | Lavie |
| 5,284,136 A | 2/1994 | Hauck et al. |
| 5,292,338 A | 3/1994 | Bardy |
| 5,299,118 A | 3/1994 | Martens et al. |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,330,505 A | 7/1994 | Cohen |
| 5,331,966 A | 7/1994 | Bennett et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,398,682 A | 3/1995 | Lynn |
| 5,411,031 A | 5/1995 | Yomtov |
| 5,411,525 A | 5/1995 | Swanson et al. |
| 5,411,539 A | 5/1995 | Neisz |
| 5,439,482 A | 8/1995 | Adams et al. |
| 5,441,518 A | 8/1995 | Adams et al. |
| 5,466,245 A | 11/1995 | Spinelli et al. |
| 5,468,254 A | 11/1995 | Hahn et al. |
| 5,483,969 A | 1/1996 | Testerman et al. |
| 5,485,851 A | 1/1996 | Erickson |
| 5,517,983 A | 5/1996 | Deighan et al. |
| 5,520,176 A | 5/1996 | Cohen |
| 5,522,382 A | 6/1996 | Sullivan et al. |
| 5,522,862 A | 6/1996 | Testerman et al. |
| 5,531,779 A | 7/1996 | Dahl et al. |
| 5,540,727 A | 7/1996 | Tockman et al. |
| 5,540,732 A | 7/1996 | Testerman |
| 5,540,734 A | 7/1996 | Zabara |
| 5,545,186 A | 8/1996 | Olson et al. |
| 5,545,202 A | 8/1996 | Dahl et al. |
| 5,549,655 A | 8/1996 | Erickson |
| 5,590,648 A | 1/1997 | Mitchell et al. |
| 5,591,216 A | 1/1997 | Testerman et al. |
| 5,603,732 A | 2/1997 | Dahl et al. |
| 5,605,151 A | 2/1997 | Lynn |
| 5,606,969 A | 3/1997 | Butler et al. |
| 5,620,466 A | 4/1997 | Haefner et al. |
| 5,622,178 A | 4/1997 | Gilham |
| 5,634,938 A | 6/1997 | Swanson et al. |
| 5,641,326 A | 6/1997 | Adams |
| 5,645,570 A | 7/1997 | Corbucci |
| 5,662,688 A | 9/1997 | Haefner et al. |
| 5,693,000 A | 12/1997 | Crosby et al. |
| 5,697,951 A | 12/1997 | Harpstead et al. |
| 5,697,953 A | 12/1997 | Kroll et al. |
| 5,701,894 A | 12/1997 | Cherry et al. |
| 5,704,365 A | 1/1998 | Albrecht et al. |
| 5,713,933 A | 2/1998 | Condie et al. |
| 5,715,812 A | 2/1998 | Deighan et al. |
| 5,724,984 A | 3/1998 | Arnold et al. |
| 5,738,102 A | 4/1998 | Lemelson |
| 5,792,188 A | 8/1998 | Starkweather et al. |
| 5,800,470 A | 9/1998 | Stein et al. |
| 5,802,188 A | 9/1998 | McDonough |
| 5,814,087 A | 9/1998 | Renirie |
| 5,826,579 A | 10/1998 | Remmers et al. |
| 5,827,326 A | 10/1998 | Kroll et al. |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,876,353 A | 3/1999 | Riff |
| 5,891,023 A | 4/1999 | Lynn |

(56) References Cited

U.S. PATENT DOCUMENTS

| | | |
|---|---|---|
| 5,895,414 A | 4/1999 | Sanchez-Zambrano |
| 5,902,250 A | 5/1999 | Verrier et al. |
| 5,911,218 A | 6/1999 | DiMarco |
| 5,916,243 A | 6/1999 | KenKnight et al. |
| 5,919,141 A | 7/1999 | Money et al. |
| 5,944,680 A | 8/1999 | Christopherson et al. |
| 5,957,956 A | 9/1999 | Kroll et al. |
| 5,961,446 A | 10/1999 | Beller et al. |
| 5,961,450 A | 10/1999 | Merchant et al. |
| 5,964,778 A | 10/1999 | Fugoso et al. |
| 5,970,975 A | 10/1999 | Estes et al. |
| 5,974,340 A | 10/1999 | Kadhiresan |
| 5,981,011 A | 11/1999 | Overcash et al. |
| 6,015,388 A | 1/2000 | Sackner et al. |
| 6,021,351 A | 2/2000 | Kadhiresan et al. |
| 6,026,320 A | 2/2000 | Carlson et al. |
| 6,044,298 A | 3/2000 | Salo et al. |
| 6,045,513 A | 4/2000 | Stone et al. |
| 6,047,203 A | 4/2000 | Sackner et al. |
| 6,050,940 A | 4/2000 | Braun et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,105,575 A | 8/2000 | Estes et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,148,230 A | 11/2000 | KenKnight |
| 6,155,976 A | 12/2000 | Sackner et al. |
| 6,161,042 A | 12/2000 | Hartley et al. |
| 6,168,568 B1 | 1/2001 | Gavriely |
| 6,181,961 B1 | 1/2001 | Prass |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,236,873 B1 | 5/2001 | Holmstrom |
| 6,240,316 B1 | 5/2001 | Richmond et al. |
| 6,251,126 B1 | 6/2001 | Ottenhoff et al. |
| 6,253,103 B1 | 6/2001 | Baura |
| 6,258,039 B1 | 7/2001 | Okamoto et al. |
| 6,259,947 B1 | 7/2001 | Olson et al. |
| 6,261,238 B1 | 7/2001 | Gavriely |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 * | 8/2001 | Hopper et al. ............... 600/513 |
| 6,277,072 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,287,264 B1 | 9/2001 | Hoffman |
| 6,303,270 B1 | 10/2001 | Flaim et al. |
| 6,306,088 B1 | 10/2001 | Krausman et al. |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,357,444 B1 | 3/2002 | Parker |
| 6,358,203 B2 | 3/2002 | Bardy |
| 6,360,127 B1 | 3/2002 | Ding et al. |
| 6,361,494 B1 | 3/2002 | Lindenthaler |
| 6,361,522 B1 | 3/2002 | Scheiner et al. |
| 6,363,270 B1 | 3/2002 | Colla et al. |
| 6,366,813 B1 | 4/2002 | DiLorenzo |
| 6,368,284 B1 | 4/2002 | Bardy |
| 6,368,287 B1 | 4/2002 | Hadas |
| 6,371,922 B1 | 4/2002 | Baumann et al. |
| 6,375,614 B1 | 4/2002 | Braun et al. |
| 6,375,621 B1 | 4/2002 | Sullivan |
| 6,375,623 B1 | 4/2002 | Gavriely |
| 6,397,845 B1 | 6/2002 | Burton |
| 6,398,728 B1 | 6/2002 | Bardy |
| 6,398,739 B1 | 6/2002 | Sullivan et al. |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,424,865 B1 | 7/2002 | Ding |
| 6,431,171 B1 | 8/2002 | Burton |
| 6,438,407 B1 | 8/2002 | Ousdigian et al. |
| 6,438,410 B2 | 8/2002 | Hsu et al. |
| 6,440,066 B1 | 8/2002 | Bardy |
| 6,442,413 B1 | 8/2002 | Silver |
| 6,449,503 B1 | 9/2002 | Hsu |
| 6,450,957 B1 | 9/2002 | Yoshimi et al. |
| 6,454,708 B1 | 9/2002 | Ferguson et al. |
| 6,459,929 B1 | 10/2002 | Hopper et al. |
| 6,463,326 B1 | 10/2002 | Hartley et al. |
| 6,468,219 B1 | 10/2002 | Njemanze |
| 6,480,733 B1 | 11/2002 | Tarcott |
| 6,487,443 B2 | 11/2002 | Olson et al. |
| 6,491,639 B1 | 12/2002 | Turcott |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,572,543 B1 | 6/2003 | Christopherson et al. |
| 6,574,507 B1 | 6/2003 | Bonnet |
| 6,580,944 B1 | 6/2003 | Katz et al. |
| 6,589,188 B1 | 7/2003 | Street et al. |
| 6,597,951 B2 | 7/2003 | Kramer et al. |
| 6,600,949 B1 | 7/2003 | Turcott |
| 6,606,993 B1 | 8/2003 | Wiesmann et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,628,986 B1 | 9/2003 | Mouchawar et al. |
| 6,638,231 B2 | 10/2003 | Govari et al. |
| 6,641,542 B2 | 11/2003 | Cho et al. |
| 6,694,186 B2 | 2/2004 | Bardy |
| 6,704,590 B2 | 3/2004 | Haldeman |
| 6,708,058 B2 | 3/2004 | Kim et al. |
| 6,723,055 B2 | 4/2004 | Hoffman |
| 6,741,885 B1 | 5/2004 | Park et al. |
| 6,752,765 B1 | 6/2004 | Jensen et al. |
| 6,752,766 B2 | 6/2004 | Kowallik et al. |
| 6,773,404 B2 | 8/2004 | Poezevera et al. |
| 6,810,287 B2 | 10/2004 | Zhu et al. |
| 6,830,548 B2 | 12/2004 | Bonnet et al. |
| 6,881,192 B1 | 4/2005 | Park |
| 6,890,306 B2 | 5/2005 | Poezevera |
| 6,892,095 B2 | 5/2005 | Salo |
| 6,904,320 B2 | 6/2005 | Park et al. |
| 6,928,324 B2 | 8/2005 | Park et al. |
| 6,964,641 B2 | 11/2005 | Cho et al. |
| 6,988,498 B2 | 1/2006 | Berthon-Jones et al. |
| 7,025,729 B2 | 4/2006 | De Chazal et al. |
| 7,025,730 B2 | 4/2006 | Cho et al. |
| 7,081,095 B2 | 7/2006 | Lynn et al. |
| 7,092,755 B2 | 8/2006 | Florio |
| 7,130,687 B2 | 10/2006 | Cho et al. |
| 7,155,278 B2 | 12/2006 | King et al. |
| 7,189,204 B2 | 3/2007 | Ni et al. |
| 7,194,313 B2 | 3/2007 | Libbus |
| 7,207,945 B2 | 4/2007 | Bardy |
| 7,225,013 B2 | 5/2007 | Geva et al. |
| 7,400,928 B2 | 7/2008 | Hatlestsad |
| 7,515,969 B2 | 4/2009 | Tockman et al. |
| 7,680,534 B2 | 3/2010 | Hopper et al. |
| 8,515,535 B2 | 8/2013 | Hopper et al. |
| 2001/0000346 A1 | 4/2001 | Ruton et al. |
| 2001/0018547 A1 | 8/2001 | Mechlenburg et al. |
| 2001/0031930 A1 | 10/2001 | Roizen et al. |

(56) References Cited

U.S. PATENT DOCUMENTS

| | | |
|---|---|---|
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082652 A1 | 6/2002 | Wentkowski et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0128563 A1 | 9/2002 | Carlson et al. |
| 2002/0138563 A1 | 9/2002 | Trivedi |
| 2002/0143264 A1 | 10/2002 | Ding et al. |
| 2002/0193839 A1 | 12/2002 | Cho et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0023184 A1 | 1/2003 | Pitts-Crick et al. |
| 2003/0036778 A1 | 2/2003 | Ostroff et al. |
| 2003/0045904 A1 | 3/2003 | Bardy et al. |
| 2003/0055348 A1 | 3/2003 | Chazal et al. |
| 2003/0055461 A1 | 3/2003 | Girouard et al. |
| 2003/0060848 A1 | 3/2003 | Kieval et al. |
| 2003/0069609 A1 | 4/2003 | Thompson |
| 2003/0088027 A1 | 5/2003 | Chin et al. |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff |
| 2003/0097153 A1 | 5/2003 | Bardy et al. |
| 2003/0100925 A1 | 5/2003 | Pape et al. |
| 2003/0153955 A1 | 8/2003 | Park et al. |
| 2003/0153956 A1 | 8/2003 | Park et al. |
| 2003/0178031 A1 | 9/2003 | Du Pen et al. |
| 2003/0187336 A1 | 10/2003 | Odagiri et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0212436 A1 | 11/2003 | Brown |
| 2003/0216789 A1 | 11/2003 | Deem et al. |
| 2004/0002742 A1 | 1/2004 | Florio |
| 2004/0030362 A1 | 2/2004 | Hill et al. |
| 2004/0059240 A1 | 3/2004 | Cho et al. |
| 2004/0088027 A1 | 5/2004 | Burnes et al. |
| 2004/0102814 A1 | 5/2004 | Sorensen et al. |
| 2004/0111040 A1 | 6/2004 | Ni et al. |
| 2004/0116981 A1 | 6/2004 | Mazar |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0176809 A1 | 9/2004 | Cho et al. |
| 2004/0210155 A1 | 10/2004 | Takemura et al. |
| 2004/0210261 A1 | 10/2004 | King et al. |
| 2004/0215240 A1 | 10/2004 | Lovett et al. |
| 2004/0230229 A1 | 11/2004 | Lovett et al. |
| 2004/0249416 A1 | 12/2004 | Yun et al. |
| 2005/0004615 A1 | 1/2005 | Sanders |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0065567 A1 | 3/2005 | Lee et al. |
| 2005/0085865 A1 | 4/2005 | Tehrani |
| 2005/0119711 A1 | 6/2005 | Cho et al. |
| 2005/0145246 A1 | 7/2005 | Hartley et al. |
| 2005/0288728 A1 | 12/2005 | Libbus et al. |
| 2007/0161873 A1 | 7/2007 | Ni et al. |
| 2007/0282215 A1 | 12/2007 | Ni et al. |

FOREIGN PATENT DOCUMENTS

| | | |
|---|---|---|
| EP | 0940155 | 9/1999 |
| EP | 1151718 | 11/2001 |
| EP | 1162125 | 12/2001 |
| EP | 1172125 | 1/2002 |
| EP | 1317943 | 6/2003 |
| JP | 3261482 | 11/1991 |
| JP | 2004/513713 A | 5/2004 |
| JP | 2005/534406 A | 11/2005 |
| JP | 2007/502670 A | 2/2007 |
| JP | 2002/345765 A | 12/2012 |
| WO | WO 84/02080 A1 | 7/1984 |
| WO | WO 92/03983 A1 | 3/1992 |
| WO | WO 92/20402 A1 | 11/1992 |
| WO | WO 99/04841 A1 | 4/1999 |
| WO | WO 00/01438 A1 | 1/2000 |
| WO | WO 00/17615 A2 | 3/2000 |
| WO | WO 02/40096 A1 | 5/2002 |
| WO | WO 02/087696 A1 | 11/2002 |
| WO | WO 2004/012815 A1 | 2/2004 |
| WO | WO 2004/049930 A2 | 6/2004 |
| WO | WO 2005/018737 A1 | 3/2005 |

OTHER PUBLICATIONS

Ajilore et al., "Nightcap: Laboratory and Home-Based Evaluation of a Portable Sleep Monitor," 32 Psychophysiology, pp. 32-98, abstract only, 1995.

Balaban et al., "Feasibility of Screening for Sleep Apnea Using Pacemaker Impedance Sensor," Cleveland Clinic, Cleveland OH, Medtronic Inc., Minneapolis, MN, Strong Memorial Hospital, Rochester New York, and Univ. Hospital, Zurich Switzerland, p. 313, 2001.

Bilgutay et al., "A New Concept in the Treatment of Hypertension Utilizing an Implantable Electronic Device: Baropacer," Trans. Am. Society Artificial Organs, vol. 10, pp. 387-395, 1964.

Bradley et al., "Cardiac Output Response to Continous Positive Airway Pressure in Congestive Heart Failure," Am. Rev. Respir. Dis., vol. 145, pp. 377-382, 1992.

Bradley et al., "Pathophysiologic and Therapeutic Implications of Sleep Apnea in Congestive Heart Failure," Journal of Cardiac Failure, vol. 2, No. 3, pp. 223-240, 1996.

Bradley et al., "Sleep Apnea and Heart Failure, Park I: Obstructive Sleep Apnea," Circulation, vol. 107, pp. 1671-1678, 2003.

Buda et al., "Effect of Intrathoracic Pressure on Left Ventricular Performance," (abstract only), 301 English Journal of Medicine, pp. 453-459, 1979.

Calvin et al., "Positive End-Expiratory Pressure (PEEP) Does Not Depress Left Ventricular Function in Patients with Pulmonary Edema," (abstract only), 124 Am. Rev. Respir. Dis., pp. 121-128, 1981.

Coleridge et al., "The Distribution, Connexions and History of Barorecptors in the Pulmonary Artery, with Some Observations on the Sensory Innervation of the ductus Arteriosus," Physiology, vol. 156, pp. 591-602, May 1961.

De Hoyos et al., "Haemodynamic Effects of Continuous Positive Airway Pressure in Humans with Normal and Impaired Left Ventricular Function," (abstract only), 88 Clin. Sci (Lond.), pp. 173-178, 1995.

(56) References Cited

OTHER PUBLICATIONS

Garrigue et al., "Benefit of Atrial Pacing in Sleep Apnea Syndrome," N. Engl. J. Med., vol. 346, No. 6, pp. 401-412, Feb. 7, 2002.

Garrigue et al., "Night Atrial Overdrive with DDD Pacing Results in a Significant Reduction of Sleep Apnea Episodes and QOL Improvement in Heart Failure Patients," Hospital Cardiologique du Haut-Leveque, University of Bordeaux, Pessac-Bordeaux, France, Abstract Session 25, p. 145, May 14, 2001.

Garrigue et al., "Night Atrial Overdrive with DDD Pacing: A new Therapy for Sleep Apnea Syndrome," Hospital Cardiologique du Haut-Leveque, University of Bordeaux, Pessac-Bordeaux, France p. 591, Apr. 2000.

Giardino et al., "Respiratory Sinus Arrhythmia is Associated with the Efficiency of Pulmonary Gas Exchange in Healthy Humans," (abstract only), Am. J. Physiology, vol. 284, H1585-1591, 2003.

Gradaus et al., "Nonthoracotomy Implantable Cardioverter Defibrillator Placement in Children: Use of a Subcutaneous Array Leads and Abdominally Placed Implantable Cardioverter Difibrillators in Children," Journal of Cardiovascular Eletrophysiology, vol. 12, No. 3, pp. 356-360, Mar. 2001.

Hanson et al., "Cardiac Gated Ventilation," SPIE, vol. 244, pp. 303-308, 1995.

Hartz et al., "New Approach to Defibrillator Insertion," Journal of Thoracic Cardiovascular Surgery, vol. 97, pp. 920-922, 1989.

Hilton et al., "Evaluation of Frequency and Time-Frequency Spectral Analysis of Heart Rate Variability as a Diagnostic Marker of the Sleep Apnea Syndrome," (abstract only), Med. Biol. Eng. Comput, vol. 37, No. 6, pp. 760-769, Nov. 1999.

International Preliminary Report on Patentability from PCT Application No. pct/us2006/006558, 8 pages, dated Sep. 20, 2007.

International Search Report and Written Opinion from PCT Application No. pct/us2006/006558, 11 pages, dated Jun. 13, 2006.

Javaheri et al., "Sleep Apnea in 81 Ambulatory Male Patients with Stable Heart Failure: types and Their Prevalences, Consequences, and Presentations," Circulation 97, No. 21, pp. 2154-2159, 1999.

Javaheri, "A Mechanism of Central Sleep Apnea in Patients with Heart Failure," New England Journal of Medicine, vol. 341, No. 13, pp. 949-954, Sep. 1999.

Kaye et al., "Acute Effects of Continous Positive Airway Pressure on Cardiac Sympathetic Tone in Congestive Heart Failure," Circulation, vol. 103, pp. 2336-24338, 2001.

Kolettis et al., "Submammary Implantation of a Cardioverter-Defibrillator with a Nonthoractomy Lead System," Am. Heart Journal, vol. 126, pp. 1222-1223, Nov. 1993.

Laude et al., "Effects of Breathing Pattern on Blood Pressure and Heart Rate Oscillations in Humans," (abstract only) 20 Clin Exp. Pharmol. Phisiol. 619, 625, 1993.

Leng et al., "Lead Configuration for Defibrillator Implantation in a Patient with Congenital Heart Disease and a Mechanical Prosthetic Tricuspid Valve," PACE, vol. 24, No. 8, pp. 1291-1292, Aug. 2001.

Lenique et al., "Ventilatory and Hemodynamic Effects of Continuous Positive Airway Pressure in Left Heart Failure," (abstract only) Am. Journal Respir. Critical Care Med., vol. 155, pp. 500-505, 1997.

Lugaresi et al., "Snoring," 39 Electroencephalogr. Clin Neurophysiol., pp. 59-64, 1975.

Mansfield et al., "Effects of Continuous Positive Airway Pressure on Lung Function in Patients with Chronic Obstructive Pulmonary Disease and Sleep Disordered Breathing," (abstract only), Respirology, pp. 365-370, 1999.

Mehta et al., "Effects of Continuous Positive Airway Pressure on Cardiac Volumes in Patients with Ischemic and Dilated Cardiomyopathy," Am. Journal of Respir. Critical Care Med., vol. 161, pp. 128-134, 2000.

Naughton et al., "Effects of Continuous Positive Airway Pressure on Intrathoracic and Left Ventricular Transmural Pressure in Congestive Heart Failure," 91 Circulation, 1725-1731, pp. 1-25, 1995.

Neil et al., "Effects of Electrical Stimulation of the Aortic Nerve on Blood Pressure and Respiration in Cats and Rabbits Under Chloralose and Nembutal Anasthesia," Journal of Physiology, vol. 109 (3-4), pp. 392-401, Sep. 1949.

Office Action from EP Application No. 06735992.7, 3 pages, Jan. 23, 2008.

Office Action from Japanese Application No. 2007-558079, 5 pages, dated Oct. 24, 2011.

Office Action from Japanese Application No. 2007-558079, 5 pages, dated May 21, 2012.

Office Action Response from EP Application No. 06735992.7, 14 pages, Nov. 4, 2008.

Office Action Response from Japanese Application No. 2007-558079, 6 pages, dated Mar. 26, 2012.

Park et al., "Use of an Implantable Cardioverter Defibrillator in an Eight-Month-Old Infant with Ventricular Fibrillation Arising from a Myocardial Fibroma," PACE, vol. 22, No. 1, pp. 138-139, Jan. 1999.

Peters et al., "Tempral and Spatial Summation Caused by Aortic Nerve Stimulation in Rabbits. Effects of Stimulation Frequencies and Amplitudes," (abstract only), Journal of the Autonomic Nervous System, vol. 27, pp. 193-205, 1989.

Pinsky et al., "Hemodynamic Effect of Cardiac Cycle-SpecificIncreases in Intrathoracic Pressure," (abstract only), Journal Appl. Physiology, vol. 6, pp. 604-612, 1986.

Potkin et al., "Effect of Positive End-Expiratory Pressure on Right and Left Ventricular Function in Patients with the Adult Respiratory Distress Syndrome," (abstract only), vol. 135, Am. Rev. Respir., Dis., pp-307-311, 1987.

Reddel et al., "Analysis of Adherence to Peak Flow Monitoring When Recording of Data is Electronic," BMJ, pp. 146-147, 2002.

Roche et al., Screening of Obstructive Sleep Apnea Syndrome by Heart Rate Variability Analysis, Circulation, 100(13), pp. 1411-1415, Sep. 1999.

Sato et al., "Novel Therapeutic Strategy Against Central Baroreflex Failure: A Bionic Baroreflex System," Circulation, vol. 100, pp. 299-304, Jul. 1999.

Satoh et al., "Role of Hypoxic Drive in Regulation of Postapneic Ventilation During Sleep in Patients with Obstructive Sleep Apnea," Am. Rev. Respir., Dis., vol. 143, No. 3, pp. 481-485, Mar. 1991.

Scharf, "Effects of Continuous Positive Airway Pressure on Cardiac Output in Experimental Heart Failure," (abstract only), 19 Sleep S240-2, 1996.

Schuder et al., "Experimental Ventricular Defibrillation with an Automatic and Completely Implanted System," Trans. Am. Soc. Artificial Int. Organs, vol. 16, pp. 207-212, 1970.

Schuder et al., "Transthoracic Ventricular Defibrillation in the Dog with Truncated and Untruncated Exponential Stimuli," IEEE Transactions on Bio-Medical Engineering, vol. BME-18, No. 6, pp. 410-415, Nov. 1971.

Schuder et al., "Ventricular Defibrillation in the Dog Using Implanted and Partially Implanted Electrode Systems," Am. Journal of Cardiology, vol. 33, pp. 243-247, Feb. 1974.

Smits et al., "Defibrillation Threshold (DFT) Model of a Fully Subcutaneous ICD System," Europace Supplements, vol. 2 at col. 778, p. B83, Jun. 2001.

Spector et al., "Assessing and Managing Dyspnea," The University of Chicago Hospitals. Nursing Spectrum—Career Fitness Online. Self-Study Modules, http://nsweb.nursingspectrum.com/, pp. 1-13.

Steltner et al., "Diagnosis of Sleep Apnea by Automatic Analysis of Nasal Pressure and Forced Oscillation Impedance," Am. Journal Respiratory Critical Care Medicine, vol. 165, pp. 940-944, 2002.

Stirbis et al., "Optimizing the Shape of Implanted Artificial Pacemakers," Kaunas Medical Institute, Translated from Meditsinskaya Tekhnika, No. 6, pp. 25-27, 1986.

Thrasher et al., "Unloading Arterial Baroreceptors Causes Neurogenic Hypertension," American Journal Physiol. Regulatory Integrative Comp. Physiol. vol. 282, R1044-R1053, 2002.

Vanninen et al., "Cardiac Sympathovagal Balance During Sleep Apnea Episodes," Clin. Physiol. vol. 16, No. 3, pp. 209-216, May 1996.

Verrier et al., Sleep Related Cardiovascular Risk: New Home-Based Monitoring Technology for Improved Diagnosis and Therapy, 2 A.N. E., pp. 158-175, 1997.

(56) References Cited

OTHER PUBLICATIONS

Verrier et al., Sleep, Dreams, and Sudden Death: the case for Sleep as an Autonomic Stress Test for the Heart, Cardiovascular Research, vol. 31, pp. 181-211, 1996.

Waldemark et al., Detection of Apnea Using Short Window FFT Technique and Artificial Neural Network, SPIE International Society for Optical Engineering, vol. 3390, pp. 122-133, 1998.

Weber et al., "Effects of CPAP and BIPAP on Stroke Volume in Patients with Obstructive Sleep Apnea Syndrome," (translated abstract only) Pneumolgie vol. 49, No. 3, pp. 233-235, Mar. 1995.

Young et al., "The Occurence of Sleep-Disordered Breathing Among Middle-Aged Adults," The New England Journal of Medicine, vol. 328, No. 17, pp. 1230-1235, Apr. 29, 1993.

\* cited by examiner

IMPLANTABLE CARDIAC DEVICE WITH DYSPNEA MEASUREMENT

RELATED PATENT DOCUMENTS

This is a continuation of U.S. patent application Ser. No. 13/967,864, filed Aug. 15, 2013, now U.S. Pat. No. 8,750,992, which is a continuation of U.S. patent application Ser. No. 12/695,895, filed Jan. 28, 2010, now U.S. Pat. No. 8,515,535, which is a divisional of U.S. patent application Ser. No. 11/067,964, filed Feb. 28, 2005, now U.S. Pat. No. 7,680,534, all of which are incorporated herein by reference.

FIELD OF THE INVENTION

The present invention relates generally to implantable cardiac devices and, more particularly, to cardiac sensing and/or stimulation devices employing dyspnea measurement.

BACKGROUND OF THE INVENTION

Dyspnea is defined as a shortness of breath or difficult breathing (the subjective feeling of being out of breath) caused by heart or lung disorders, strenuous activity, high anxiety or stress. Dyspnea derives from interactions among multiple physiological, psychological, social, and environmental factors, and may induce secondary physiological and behavioral responses. Dyspnea is different from tachypnea (rapid breathing) and hyperpnea (deep breathing). Tachypnea and hyperpnea can occur with hyperventilation, or over breathing beyond what is required to maintain arterial blood gases within normal limits. Fear or anxiety may create even more distress in dyspneic patients.

Clinically, a dyspnea index has been developed as a monitoring tool for dyspnea. One conventional method of determining a dyspnea index value has a subject take a deep breath in and count out loud from 1 to 15 (should take approximately 8 seconds). When stressed or running out of air, the subject stops counting, takes another deep breath and then continues counting from where they left off. This is repeated as needed until the subject finishes counting to 15. The number of breaths needed to take in addition to the very first one is the dyspnea index.

Using the subject's dyspnea index measurement, a value of 0-1 is considered normal. A dyspnea value of 2-3 is acceptable, depending on what activity is being performed. At a dyspnea value of 4, the subject should slow down, and think about stopping. At a dyspnea value of 5, the subject should definitely stop and rest.

Dyspnea may be classified as chronic, acute, or terminal. Chronic dyspnea has a variable intensity and persistent shortness of breath. This is most often seen in patients with chronic obstructive pulmonary disease (COPD). Acute dyspnea causes episodes of shortness of breath with high intensity. It may be seen in patients who have suffered a myocardial infarction or pulmonary embolism. Terminal dyspnea occurs in patients with end-stage diseases, and these patients may be in a hospital, at home, or in a hospice. This type of dyspnea is a common complaint in patients with cancer. Dyspnea can be caused by a variety of conditions, including metabolic, allergic, psychiatric, and neuromuscular disorders, and by pain. However, cardiac and pulmonary disorders are the most common causes.

To manage dyspnea, nonpharmacological and pharmacological interventions may be performed. For example, treating patients in cardiac failure with digoxin and diuretics may resolve the problem. Stimulation of mechanoreceptors in the respiratory musculature or over the face has reduced dyspnea in some patients. Vibration of the intercostal muscles, in phase with inspiration so that contracting respiratory muscles are vibrated, has relieved dyspnea in some COPD patients. This intervention has worked best with severe dyspnea at rest. Movement of cool air across the face by a fan or an open window can stimulate mechanoreceptors in the face, minimizing mild dyspnea.

Patients with COPD often obtain relief from dyspnea while sitting and leaning forward with their arms supported on a table. Unsupported arm and shoulder movement alters the efficient use of respiratory muscles. This position may also improve overall inspiratory muscle strength and enhance the efficiency of diaphragmatic breathing. Techniques like pursed-lip and diaphragmatic breathing are widely used to reduce dyspnea in COPD patients, though their effect is variable. These breathing techniques allow for slower and deeper breathing, thus raising tidal volume and decreasing respiratory rates. Pursed-lip breathing is especially useful for patients with emphysema because it creates positive end-expiratory pressure in the alveoli, thus splinting airways that have lost their collagen matrix. However, patients often revert to their fast and shallow breathing patterns, which may be compensatory for the mechanism causing dyspnea.

Oxygen, administered by mask or nasal cannula or transtracheally, improves dyspnea. In patients with COPD, most authorities recommend oxygen therapy for raising PaO2 levels to at least 55 mmHg to 60-mmHg or oxygen saturation to 88% to 90%.

Evidence suggests that opioids, despite their possible respiratory depressant effect, are useful in managing dyspnea. While the action of opioids to relieve dyspnea is not fully understood, the drugs may act by blunting the emotional reaction to dyspnea by interaction with opioid receptors in the limbic system. Because opioids cause euphoria, they reduce fear, anxiety, and the associated restlessness and muscle tension that decrease oxygen consumption. Opioids may also relieve dyspnea by action on the chemoreceptors, thus reducing respiratory drive.

When the dyspnea becomes intolerable and increased doses of systemic opioids are contraindicated because of unacceptable adverse effects, nebulized morphine may be started. Nebulized morphine may relieve dyspnea by direct local action on peripheral opioid receptors in the airways so that it does not reach the systemic concentration to the extent that oral, subcutaneous, or intravenous morphine does. Therefore, some patients experience relief of dyspnea with fewer adverse effects.

Anxiolytics frequently used to relieve dyspnea include benzodiazepines and phenothiazines. These act by depressing the hypoxic, hypercapnic response to dyspnea and the emotional response to dyspnea. Depending on the cause of dyspnea, patients may benefit from bronchodilators. Since methylxanthines cause smooth muscle dilation of the airways and improve the contraction of the diaphragm, they may be useful in patients with COPD. Similarly, inhaled beta-2 adrenergic agonists and anticholinergics cause smooth muscle dilation of the airways, thus improving lung mechanics and possibly relieving dyspnea.

SUMMARY OF THE INVENTION

The present invention is directed to cardiac monitoring and/or stimulation methods and systems that provide monitoring, defibrillation therapies, pacing therapies, or a combination of these capabilities. Embodiments of the present invention relate generally to implantable medical devices employing dyspnea measurement and/or detection capability.

Embodiments of methods in accordance with the present invention involve providing an implantable cardiac device configured to sense transthoracic impedance and determine a patient activity level. An index indicative of pulmonary function is implantably computed using the sensed transthoracic impedance. An episode of dyspnea may be detected based on a change in a computed pulmonary function index exceeding a threshold at a determined patient activity level.

Further embodiments are directed to methods that trend one or more pulmonary function index values to determine a patient's pulmonary function index profile. The threshold for detecting the dyspnea episode may be based on the patient's pulmonary function index profile. Other embodiments may involve trending one or more pulmonary function index values and their associated patient activity levels to determine a patient's pulmonary function index versus activity level profile.

The threshold for detecting the dyspnea episode may be based on the patient's pulmonary function index versus activity level profile by computing the pulmonary function index as a ratio of a respiratory rate value and a tidal volume value for a patient. Methods may further involve adapting a cardiac therapy for the patient based on a pulmonary function index value. An adapted cardiac therapy may be delivered to the patient after comparing the pulmonary function index value to a threshold and determining the pulmonary function index value is beyond the threshold. Adapting the cardiac therapy may also involve comparing the pulmonary function index value to a predetermined range and modifying the cardiac therapy if the pulmonary function index value is beyond the predetermined range. Therapy adaptations include increasing or decreasing a rate at which pacing pulses are delivered to the patient's heart, for example increasing or decreasing pacing pulses within a range of about 5 to about 10 beats per minute.

Methods may further involve determining a patient's sleep-state at least in part using the pulmonary function index and/or a trend of pulmonary function index values. A physician may be automatically alerted in response to a pulmonary function index value and/or a trend of the patient's pulmonary index being beyond a threshold. Computed pulmonary function index values and their associated patient's activity levels may be stored periodically in a memory and/or transmitted to a patient-external device.

Devices in accordance with the present invention include a sensor configured to sense transthoracic impedance. A controller is coupled to the sensor and configured to compute an index indicative of pulmonary function using the sensed transthoracic impedance. An activity sensor is also coupled to the controller and configured to sense patient activity. Therapy circuitry is coupled to the controller and configured to provide a therapy at least partly based on a computed pulmonary function index value and a sensed patient activity level. An electrode may be coupled to the cardiac therapy circuitry and configured to deliver the cardiac therapy.

The pulmonary function index may be a dyspnea index, computed as a ratio of a respiration rate to a tidal volume. Memory may be coupled to the controller and configured to store periodically computed pulmonary function index values and their associated patient activity levels. Communications circuitry may also be coupled to the controller and configured to communicate pulmonary function index values and/or their associated patient activity levels to a patient-external device. The device may further provide alerts to the patient and/or physician, such as by using a patient-external device or an advanced patient management system.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
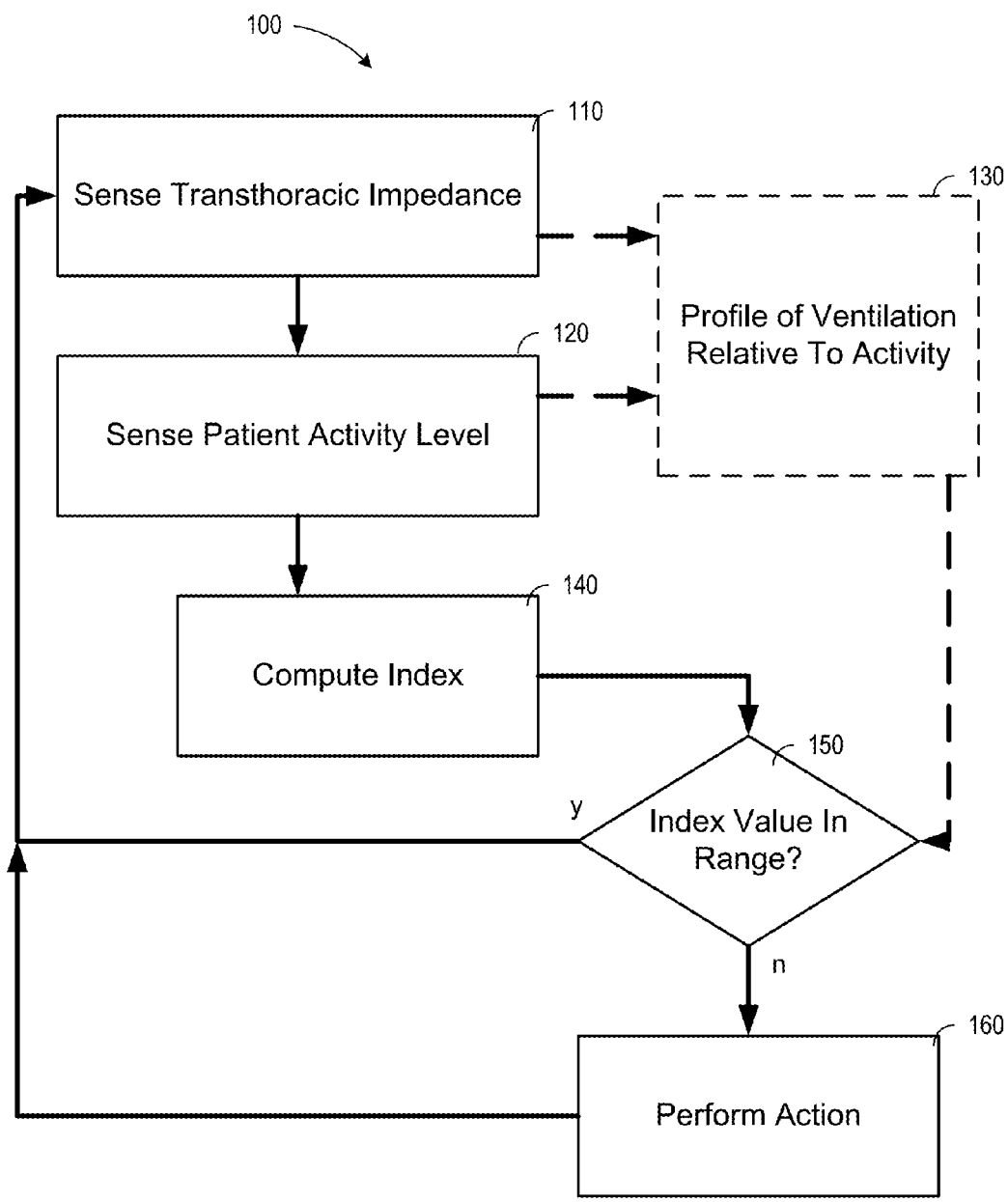
FIG. 1 is a block diagram of embodiments of methods for controlling patient implanted medical devices incorporating dyspnea measurements in accordance with the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable cardiac sensing and/or stimulation devices may be configured to implement a dyspnea measurement methodology of the present invention. A non-limiting, representative list of such devices includes cardiac monitors, pacemakers, cardiovertors, defibrillators, resynchronizers, and other cardiac sensing and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac devices, such as those listed above, and are referred to herein generally as a patient implantable medical device (PIMD) for convenience. A PIMD implemented in accordance with the present invention may incorporate one or more of the electrode types identified above and/or combinations thereof.

Many patients implanted with a pacemaker/defibrillator/CRT device have minute ventilation changes that reflect a change in the patient's cardiopulmonary function. A decrease in cardiopulmonary function often manifests itself in a form of dyspnea (shortness of breath). Typically, dyspnea can be seen both at rest and during exercise.

The pulmonary characteristics of a patient that a physician typically evaluates may be described using a dyspnea scale. The dyspnea scale relates the pulmonary parameters of respiratory rate (RR), in breaths per minute, to tidal volume (Vt), in milliliters per minute or liters per minute. A pulmonary index, such as may be obtained by dividing the respiratory rate by the tidal volume, (RR/Vt) for example, gives the physician an evaluation tool for dyspnea measurement. The pulmonary index may be used to detect a dyspnea episode in which the patient has an increased RR confirmed by a decreased Vt.

Typically, changes in a patient's cardiopulmonary response after a pacemaker has been implanted are not addressed until the patient is symptomatic, and has gone through a formal clinical evaluation with the use of external gas exchange equipment. A PIMD having dyspnea measurement capabilities in accordance with the present invention reduces the response time needed to correct the patient's dyspnea problem and/or to introduce additional therapy. A PIMD having dyspnea measurement capabilities in accordance with the present invention may also provide trending of the patient's dyspnea over time.

A PIMD that incorporates dyspnea measurement in accordance with the present invention may be implanted in a patient. The PIMD may sense, for example, transthoracic impedance and patient activity. Parameters, such as respiration rate, minute ventilation, and tidal volume, may be detected along with activity levels of the patient associated with the measured parameters.

Patient profiles may be established, to determine what levels of a particular parameter occur for a given activity level, time of day, or the like. Indexes may be established, such as an RR/Vt index. As a patient is resting, performing moderate exercise, or performing maximum exertion, baselines for patient parameters and/or index values may be determined and recorded in the PIMD.

Changes in parameters and index values may be used to trigger alerts, modify therapies, or otherwise control the PIMD. Parameters and index values may be displayed to the patient on a patient-external monitor, so that the patient may evaluate and/or modify their behavior. If a dyspnea index value is too high, the PIMD may increase the heart rate a modest amount, for example 5 to 10 beats per minute, to adapt the heart rate to the patient's need for oxygen. PIMDs that incorporate adaptive dyspnea control may provide improved patient performance and less physician intervention than other PIMDs.

In another embodiment of the present invention, a PIMD with dyspnea detection capability may develop a model of the cardiopulmonary response of an individual patient to track changes in a patient's condition. Patients whose cardiopulmonary status deteriorates over time can be easily evaluated without the use of external gas exchange equipment. The physician may be alerted to changes in the patient's status, thereby reducing the length and intensity of dyspnea that a patient experiences before intervention.

FIG. 1 is a block diagram of embodiments of a method 100 for controlling patient implanted medical devices incorporating dyspnea measurements in accordance with the present invention. The method 100 includes a block 110 providing for the sensing of a patient's breathing, such as by using transthoracic impedance to determine respiration rate and tidal volume. A block 120 provides for the sensing of the patient's activity level, such as by using an accelerometer, an EMG sensor, an EEG sensor, or other patient activity level sensing methodology. Measured parameters, such as respiration rate, minute ventilation, activity level, and/or statistical analyses of measured parameters may be used at a block 140 to compute one or more index indicative of the patient's cardiopulmonary status. The index value from block 140 is compared at a decision block 150 to determine if some action is necessary. For example, an index value may be compared to an acceptable range, to determine if the value lies within an expected or acceptable range. In another example, the rate of change of the index value may be compared to an acceptable rate of change, to determine if the value lies within an expected or acceptable range. If the index value is acceptable, the method 100 returns to the block 110 for subsequent sensing and determinations. If the index value is not acceptable, an action 160 may be performed to attempt to bring the patient to an acceptable cardiopulmonary function, alert the patient or physician, or perform other appropriate actions before returning to the block 110.

In a further embodiment of the method 100, optionally or additionally, a profile 130 may be used to determine the cardiopulmonary condition of the patient. The blocks 110, 120 may provide sensing information to the profile 130. The profile 130 may use, for example, look-up tables of index values for ranges of patient activity, which may be useful for determining if the patient requires some form of action 160, or if the sensed parameters are expected for the patient. Profile information may be used exclusively in the determination 150, or combined with information from the index computed at block 140.

Figure 2:
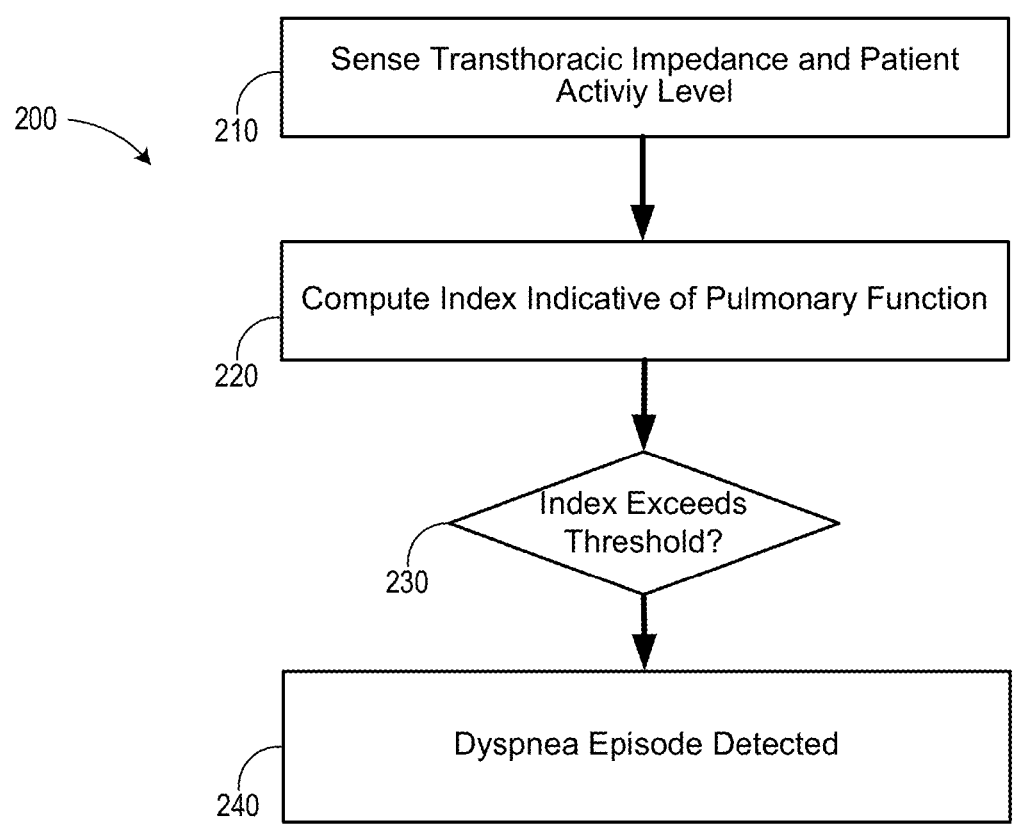
FIG. 2 is a block diagram of a dyspnea determination method in accordance with the present invention.

FIG. 2 is a block diagram of a dyspnea determination method 200 in accordance with the present invention. Transthoracic impedance and patient activity level are sensed at a block 210. Transthoracic impedance and patient activity level measurements from the block 210 are used to compute one or more index vale indicative of pulmonary function at a block 220.

The index value from the block 220 is compared, at a decision 230, to determine if the index value is beyond an acceptable threshold. If the index value is beyond the threshold, a dyspnea episode is detected at block 240. For example, a dyspnea index may be computed at block 220 by dividing the patient's respiratory rate by the patient's tidal volume (RR/Vt).

At a dyspnea index value above 3, the patient's PIMD may be adapted by increasing the patient's heart rate 5-10 beats per minute. At a dyspnea index value above 4, the patient's PIMD may further increase the patient's heart rate, and/or may alert the patient to a potential problem. At a dyspnea index value above 5, the patient's PIMD may alert emergency response services to respond to the patient's needs. It is understood that the index values above represent potential values based on calculation coefficients for the particular index, and that ranges of index values may be established clinically and/or individually for each patient and/or each index. It is also understood that the actions described above associated with the index values are for purposes of illustration only, and are not intended as limiting descriptions.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of a type that may benefit from dyspnea measuring methods and implementations are disclosed in commonly owned U.S. Pat. Nos. 5,133,353; 5,179, 945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of a type that may benefit from dyspnea measuring methods and implementations are disclosed in commonly owned U.S. Pat. Nos. 4,562,841; 5,284,136; 5,376,106; 5,036,849; 5,540,727; 5,836,987; 6,044,298; and 6,055,454, which are hereby incorporated by reference. It is understood that PIMD configurations may provide for non-physiologic pacing support in addition to, or to the exclusion of, bradycardia and/or anti-tachycardia pacing therapies.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of a type that may benefit from dyspnea measuring methods and implementations are disclosed in commonly owned U.S. Pat. Nos. 5,313, 953; 5,388,578; and 5,411,031, which are hereby incorporated herein by reference.

Various embodiments described herein may be used in connection with congestive heart failure (CHF) monitoring, diagnosis, and/or therapy. A PIMD of the present invention may incorporate CHF features involving dual-chamber or bi-ventricular pacing/therapy, cardiac resynchronization therapy, cardiac function optimization, or other CHF related methodologies. For example, a PIMD of the present invention may incorporate features of one or more of the following references: commonly owned U.S. patent application Ser. No. 10/270,035, now U.S. Pat. No. 7,260,432 and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

Figure 3:
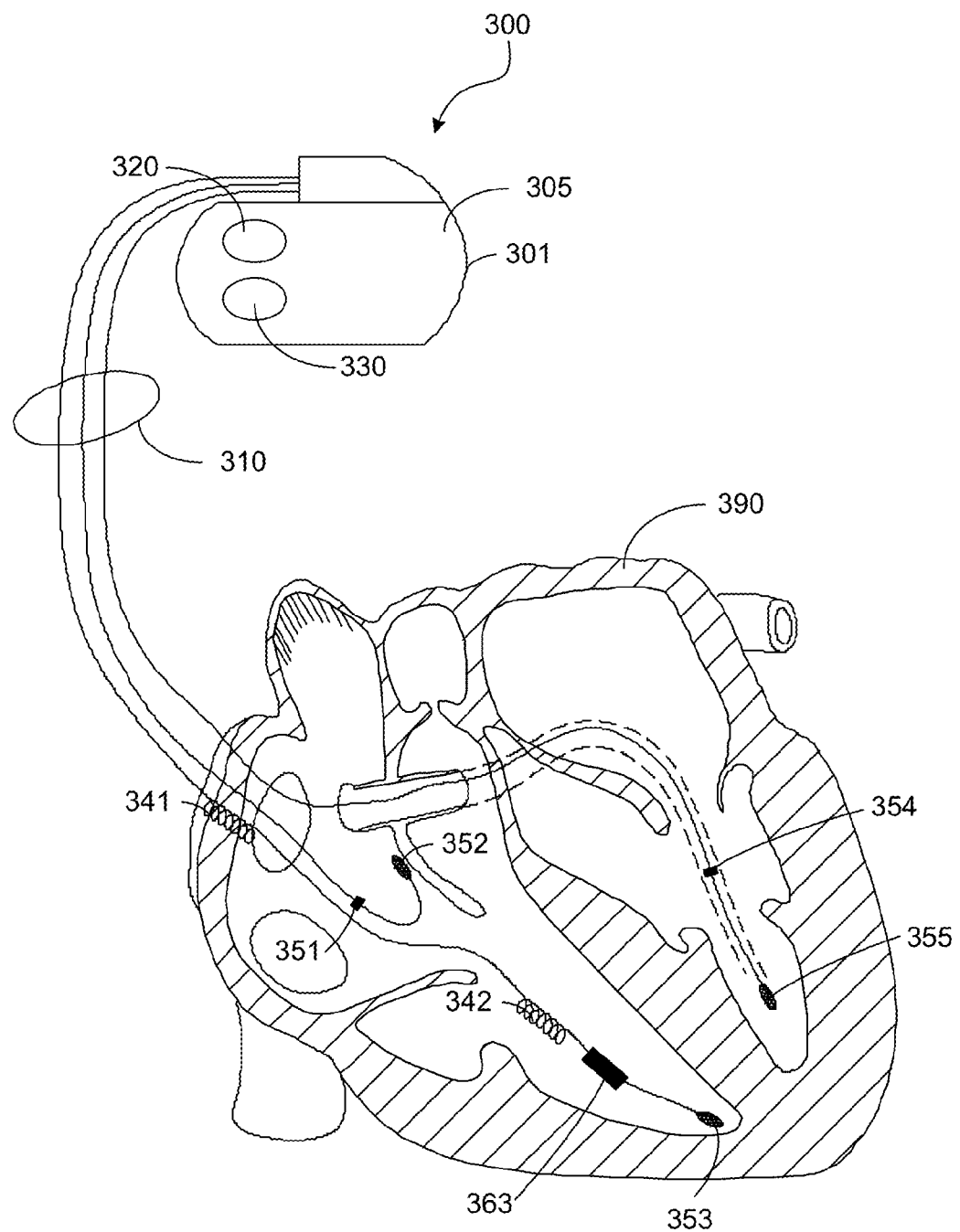
FIG. 3 is an illustration of an implantable cardiac device including a lead assembly shown implanted in a sectional view of a heart, in accordance with embodiments of the invention.

Referring now to FIG. 3, the implantable device illustrated in FIG. 3 is an embodiment of a PIMD configured to determine dyspnea in accordance with the present invention. In this example, the implantable device includes a cardiac rhythm management device (CRM) 300 including an implantable pulse generator 305 electrically and physically coupled to an intracardiac lead system 310.

Portions of the intracardiac lead system 310 are inserted into the patient's heart 390. The intracardiac lead system 310 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 301 of the pulse generator 305 may optionally serve as a can electrode.

Communications circuitry is disposed within the housing 301 for facilitating communication between the pulse generator 305 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 305 may optionally incorporate a motion detector 320 that may be used to sense patient activity as well as various respiration and cardiac related conditions. For example, the motion detector 320 may be optionally configured to sense snoring, activity level, and/or chest wall movements associated with respiratory effort, for example. The motion detector 320 may be implemented as an accelerometer positioned in or on the housing 301 of the pulse generator 305. If the motion sensor is implemented as an accelerometer, the motion sensor may also provide respiratory, e.g. rales, coughing, and cardiac, e.g. S1-S4 heart sounds, murmurs, and other acoustic information.

The lead system 310 and pulse generator 305 of the CRM 300 may incorporate one or more transthoracic impedance sensors that may be used to acquire the patient's respiration waveform, or other respiration-related information. The transthoracic impedance sensor may include, for example, one or more intracardiac electrodes 341, 342, 351-355, 363 positioned in one or more chambers of the heart 390. The intracardiac electrodes 341, 342, 351-355, 363 may be coupled to impedance drive/sense circuitry 330 positioned within the housing of the pulse generator 305.

In one implementation, impedance drive/sense circuitry 330 generates a current that flows through the tissue between an impedance drive electrode 351 and a can electrode on the housing 301 of the pulse generator 305. The voltage at an impedance sense electrode 352 relative to the can electrode changes as the patient's transthoracic impedance changes. The voltage signal developed between the impedance sense electrode 352 and the can electrode is detected by the impedance sense circuitry 330. Other locations and/or combinations of impedance sense and drive electrodes are also possible.

The lead system 310 may include one or more cardiac pace/sense electrodes 351-355 positioned in, on, or about one or more heart chambers for sensing electrical signals from the patient's heart 390 and/or delivering pacing pulses to the heart 390. The intracardiac sense/pace electrodes 351-355, such as those illustrated in FIG. 3, may be used to sense and/or pace one or more chambers of the heart, including the left ventricle, the right ventricle, the left atrium and/or the right atrium. The lead system 310 may include one or more defibrillation electrodes 341, 342 for delivering defibrillation/cardioversion shocks to the heart.

The pulse generator 305 may include circuitry for detecting cardiac arrhythmias and/or for controlling pacing or defibrillation therapy in the form of electrical stimulation pulses or shocks delivered to the heart through the lead system 310. The pulse generator 305 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

For purposes of illustration, and not of limitation, various embodiments of devices that may use dyspnea measurement in accordance with the present invention are described herein in the context of PIMD's that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. patent application Ser. No. 10/465,520 filed Jun. 19, 2003, now U.S. Publication No. 2004/0230230 and Ser. No. 10/738,608 filed Dec. 17, 2003, now U.S. Pat. No. 7,499,750, which are hereby incorporated herein by reference.

Figure 4:
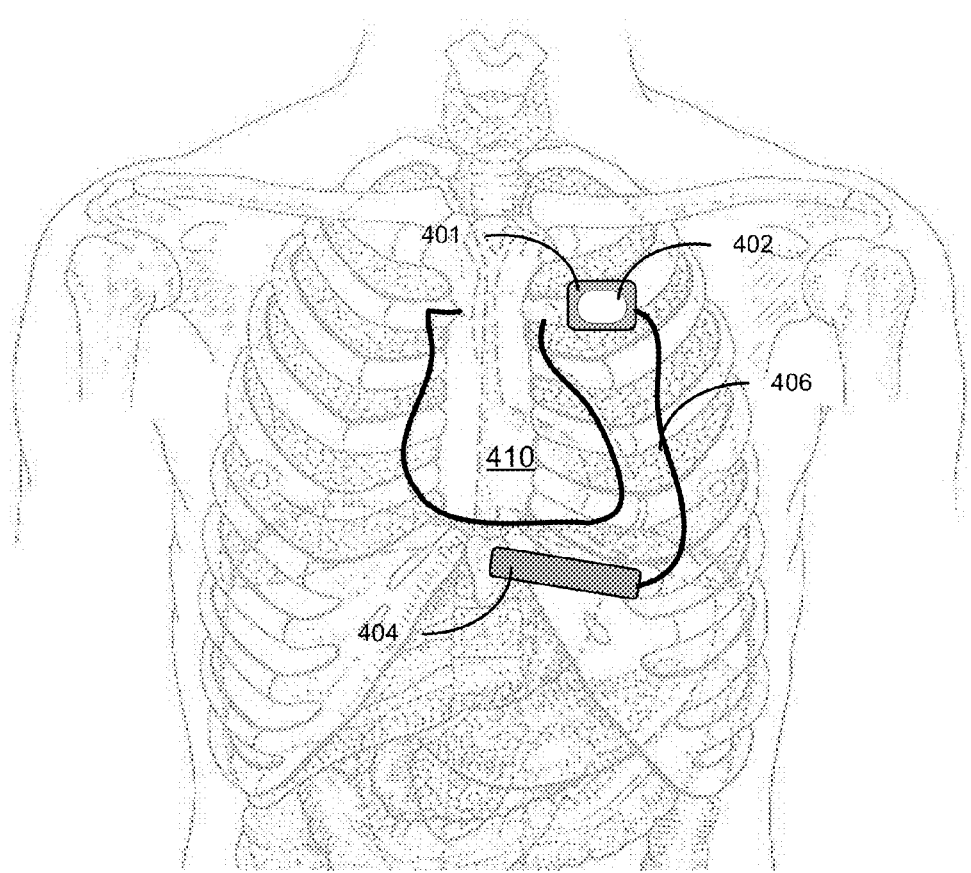
FIG. 4 is a diagram illustrating components of a cardiac sensing and/or stimulation device including an electrode array in accordance with an embodiment of the present invention.

In one configuration, as is illustrated in FIG. 4, electrode subsystems of a PIMD system are arranged about a patient's heart 410. The PIMD system includes a first electrode subsystem, comprising a can electrode 402, and a second electrode subsystem 404 that includes at least two electrodes or at least one multi-element electrode. The second electrode subsystem 404 may include a number of electrodes used for sensing and/or electrical stimulation.

In various configurations, the second electrode subsystem 404 may include a combination of electrodes. The combination of electrodes of the second electrode subsystem 404 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 402 is positioned on the housing 401 that encloses the PIMD electronics. In one embodiment, the can electrode 402 includes the entirety of the external surface of housing 401. In other embodiments, various portions of the housing 401 may be electrically isolated from the can electrode 402 or from tissue. For example, the active area of the can electrode 402 may include all or a portion of either the anterior or posterior surface of the housing 401 to direct current flow in a manner advantageous for cardiac sensing and/or stimulation.

In accordance with one embodiment, the housing 401 may resemble that of a conventional implantable PIMD, is approximately 20-100 cc in volume, with a thickness of 0.4 to 2 cm and with a surface area on each face of approximately 30 to 100 cm². As previously discussed, portions of the housing may be electrically isolated from tissue to optimally direct current flow. For example, portions of the housing 401 may be covered with a non-conductive, or otherwise electrically resistive, material to direct current flow. Suitable non-conductive material coatings include those formed from silicone rubber, polyurethane, or parylene, for example.

Figure 5:
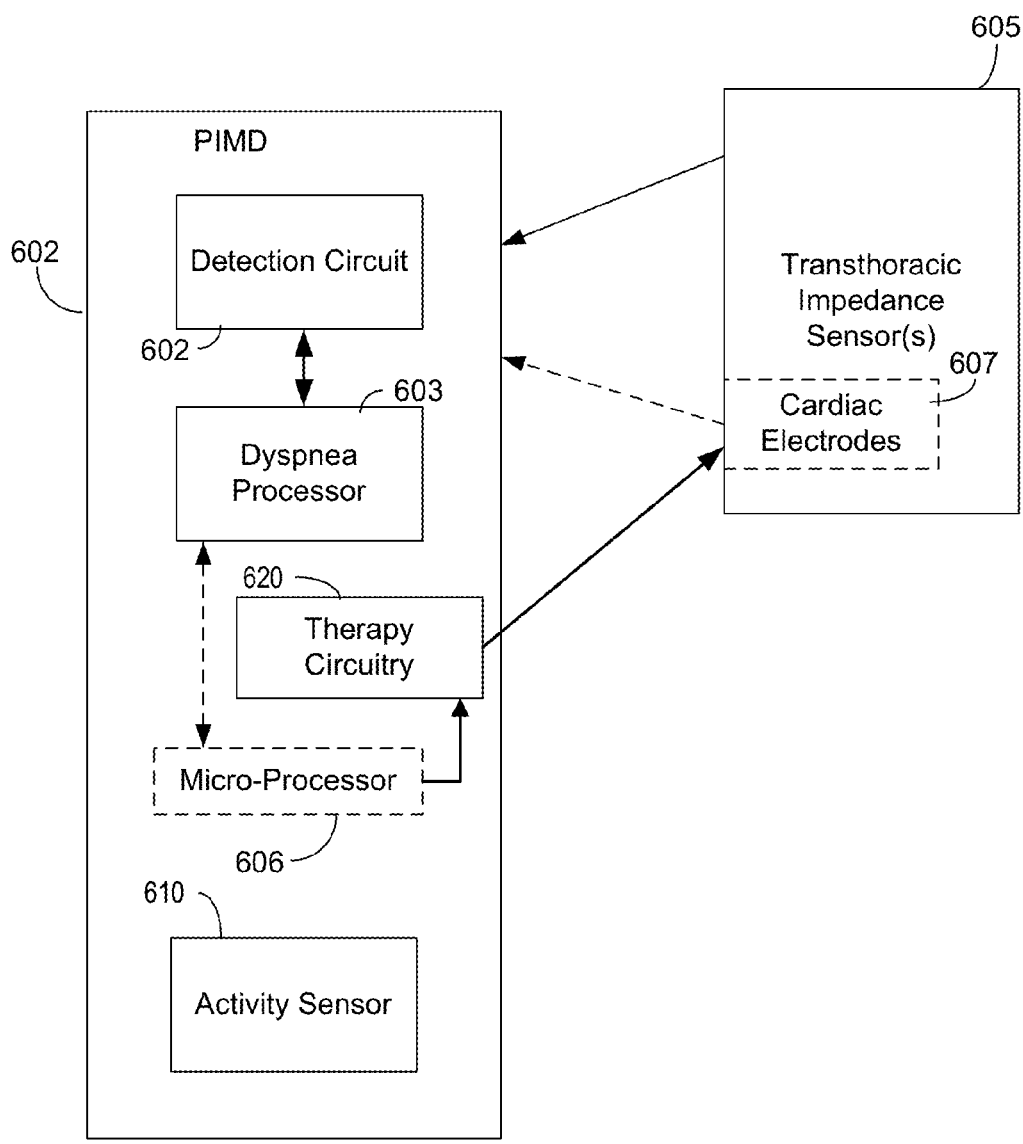
FIG. 5 is a block diagram illustrating various processing and detection components of a cardiac sensing and/or stimulation device in accordance with an embodiment of the present invention.

FIG. 5 illustrates a block diagram of a PIMD 602, which includes a dyspnea processor 603 which may be incorporated into and/or work in cooperation with a microprocessor 606. A detection circuit 602, which may be coupled to the dyspnea processor 603 and/or the microprocessor 606, may be configured to incorporate, or communicate with, specialized circuitry for processing sensed cardiac signals in manners particularly useful in a cardiac sensing and/or stimulation device. As is shown by way of example in FIG. 5, the detection circuitry 602 may receive information from multiple physiologic and non-physiologic sensors.

The detection circuitry 602 receives information from one or more sensor(s) 605 that monitor transthoracic impedance. As is known in the art, transthoracic impedance sensor(s) 605 may be the same as or different from one or more cardiac electrodes 607 used for cardiac sensing and/or stimulation. The dyspnea processor 603 is coupled to the sensor(s) 605 and configured to compute an index indicative of pulmonary function using the sensed transthoracic impedance. An activity sensor 610 is coupled to the dyspnea processor 603 and configured to sense patient activity. The activity sensor 610 may be, for example, an accelerometer in, on, or coupled to the PIMD 602. Therapy circuitry 620 is coupled to the microprocessor 606 and configured to provide a therapy at least partly based on a computed pulmonary function index value and a sensed patient activity level determined by the dyspnea processor 603. Therapy circuitry 620 is coupled to one or more of the cardiac electrodes 607 and configured to deliver a cardiac therapy.

Figure 6:
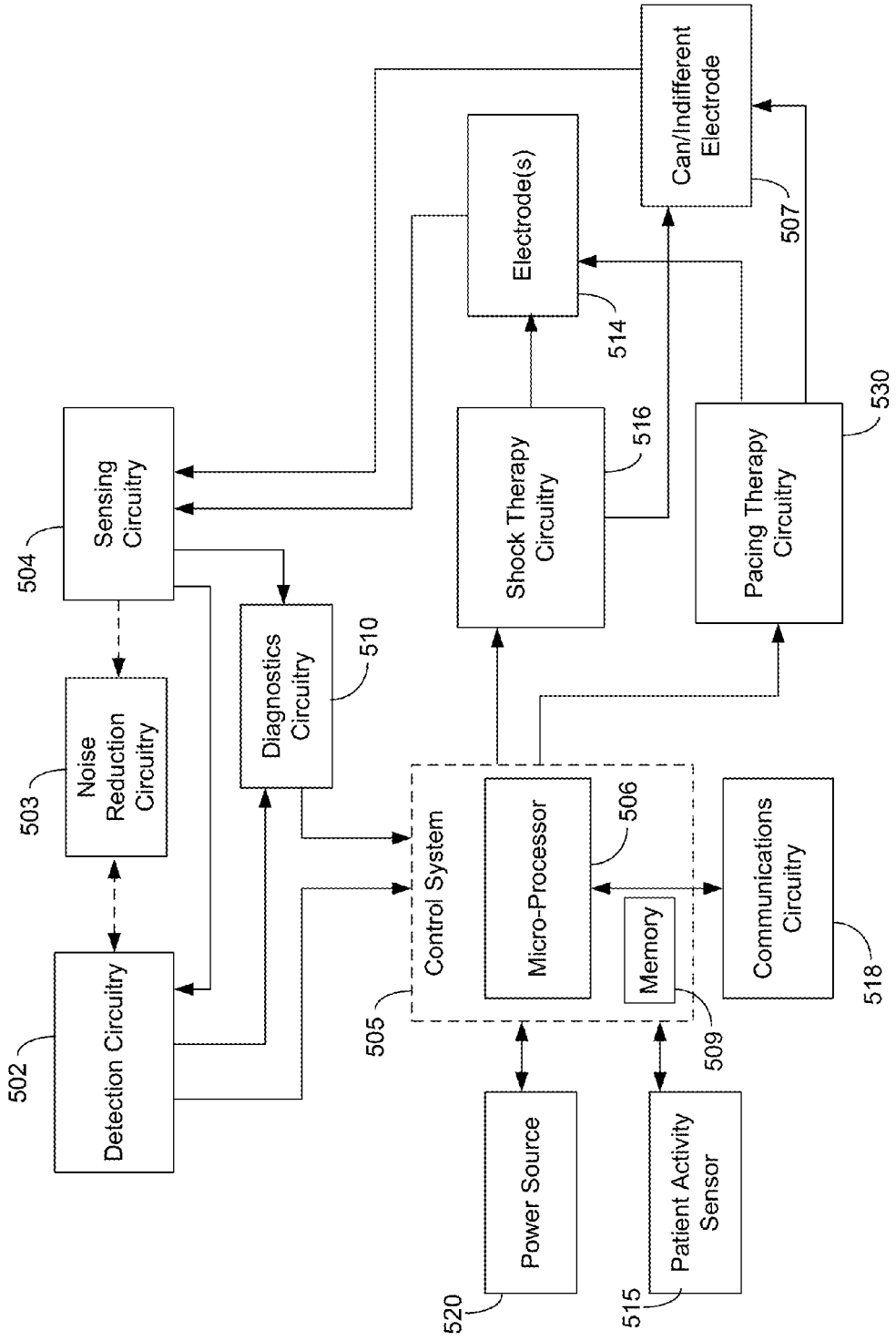
FIG. 6 is a block diagram illustrating various components of a cardiac sensing and/or stimulation device in accordance with an embodiment of the present invention.

FIG. 6 is a block diagram depicting various components of a PIMD in accordance with one configuration. According to this configuration, the PIMD incorporates a processor-based control system 505 that includes a microprocessor 506 coupled to appropriate memory (volatile and non-volatile) 509, it being understood that any logic-based control architecture may be used. The control system 505 is coupled to circuitry and components to sense, detect, and analyze electrical signals produced by the heart and deliver electrical stimulation energy to the heart under predetermined conditions to treat cardiac arrhythmias. The control system 505 and associated components also provide pacing therapy to the heart. The electrical energy delivered by the PIMD may be in the form of low energy pacing pulses or high-energy pulses for cardioversion or defibrillation.

Cardiac signals are sensed using the electrode(s) 514 and the can or indifferent electrode 507 provided on the PIMD housing. Cardiac signals may also be sensed using only the electrode(s) 514, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 504, which includes sense amplification circuitry and may also include filtering circuitry and an analog-to-digital (A/D) converter. The sensed cardiac signals processed by the sensing circuitry 504 may be received by noise reduction circuitry 503, which may further reduce noise before signals are sent to the detection circuitry 502.

Noise reduction circuitry 503 may also be incorporated after sensing circuitry 502 in cases where high power or computationally intensive noise reduction algorithms are required. The noise reduction circuitry 503, by way of amplifiers used to perform operations with the electrode signals, may also perform the function of the sensing circuitry 504. Combining the functions of sensing circuitry 504 and noise reduction circuitry 503 may be useful to minimize the necessary componentry and lower the power requirements of the system.

Patient activity may be sensed by a patient activity sensor 515, coupled to the microprocessor 506, to provide patient activity information. The patient activity information may be used by the microprocessor 506 to determine a pulmonary function index value as described above.

In the illustrative configuration shown in FIG. 6, the detection circuitry 502 is coupled to, or otherwise incorporates, noise reduction circuitry 503. The noise reduction circuitry 503 operates to improve the SNR of sensed cardiac signals by removing noise content of the sensed cardiac signals introduced from various sources. Detection circuitry 502 includes a signal processor that coordinates analysis of the sensed cardiac signals, patient activity information, and transthoracic impedance signals to detect dyspnea in accordance with embodiments of the present invention.

Rate based and/or morphological discrimination algorithms may be implemented by the signal processor of the detection circuitry 502 to detect and verify the presence and severity of an arrhythmic episode. Examples of arrhythmia detection and discrimination circuitry, structures, and techniques, aspects of which may be implemented by a PIMD of a type that may benefit from dyspnea measuring methods and implementations are disclosed in commonly owned U.S. Pat. Nos. 5,301,677, 6,438,410, and 6,708,058, which are hereby incorporated herein by reference. Arrhythmia detection methodologies particularly well suited for implementation in cardiac monitoring and/or stimulation systems are described hereinbelow.

The detection circuitry 502 communicates cardiac signal information to the control system 505. Memory circuitry 509 of the control system 505 contains parameters for operating in various sensing, defibrillation, and, if applicable, pacing modes, and stores data indicative of cardiac signals received by the detection circuitry 502. The memory circuitry 509 may also be configured to store historical ECG and therapy data, patient activity data, pulmonary function index data, and/or dyspnea information, which may be used for various purposes and transmitted to an external receiving device as needed or desired.

In certain configurations, the PIMD may include diagnostics circuitry 510. The diagnostics circuitry 510 typically receives input signals from the detection circuitry 502 and the sensing circuitry 504. The diagnostics circuitry 510 provides diagnostics data to the control system 505, it being understood that the control system 505 may incorporate all or part of the diagnostics circuitry 510 or its functionality. The control system 505 may store and use information provided by the diagnostics circuitry 510 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 505 processes cardiac signal data received from the detection circuitry 502 and initiates appropriate tachyarrhythmia therapies to terminate cardiac arrhythmic episodes and return the heart to normal sinus rhythm. The control system 505 is coupled to shock therapy circuitry 516. The shock therapy circuitry 516 is coupled to the electrode(s) 514 and the can or indifferent electrode 507 of the PIMD housing. Upon command, the shock therapy circuitry 516 delivers cardioversion and defibrillation stimulation energy to the heart in accordance with a selected cardioversion or defibrillation therapy. In a less sophisticated configuration, the shock therapy circuitry 516 is controlled to deliver defibrillation therapies, in contrast to a configuration that provides for delivery of both cardioversion and defibrillation therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

In accordance with another configuration, a PIMD may incorporate a cardiac pacing capability in addition to, or to the exclusion of, cardioversion and/or defibrillation capabilities. As is shown in FIG. 6, the PIMD includes pacing therapy circuitry 530 that is coupled to the control system 505 and the electrode(s) 514 and can/indifferent electrodes 507. Upon command, the pacing therapy circuitry 530 delivers pacing pulses to the heart in accordance with a selected pacing therapy. Control signals, developed in accordance with a pacing regimen by pacemaker circuitry within the control system 505, are initiated and transmitted to the pacing therapy circuitry 530 where pacing pulses are generated. A pacing regimen, such as those discussed and incorporated herein, may be modified by the control system 505.

The PIMD shown in FIG. 6 may be configured to receive signals from one or more physiologic and/or non-physiologic sensors. Depending on the type of sensor employed, signals generated by the sensors may be communicated to transducer circuitry coupled directly to the detection circuitry 502 or indirectly via the sensing circuitry 504. It is noted that certain sensors may transmit sense data to the control system 505 without processing by the detection circuitry 502.

Communications circuitry 518 is coupled to the microprocessor 506 of the control system 505. The communications circuitry 518 allows the PIMD to communicate with one or more receiving devices or systems situated external to the PIMD. By way of example, the PIMD may communicate with a patient-worn, portable or bedside communication system via the communications circuitry 518. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD via the communications circuitry 518. It is noted that physiologic or non-physiologic sensors equipped with wireless transmitters or transceivers may communicate with a receiving system external of the patient.

The communications circuitry 518 preferably allows the PIMD to communicate with an external programmer. In one configuration, the communications circuitry 518 and the programmer unit (not shown) use a wire loop antenna and a radio frequency telemetric link, as is known in the art, to receive and transmit signals and data between the programmer unit and communications circuitry 518. In this manner, programming commands and data are transferred between the PIMD and the programmer unit during and after implant. Using a programmer, a physician is able to set or modify various parameters used by the PIMD. For example, a physician may set or modify parameters affecting sensing, detection, pacing, and defibrillation functions of the PIMD, including pacing and cardioversion/defibrillation therapy modes.

Typically, the PIMD is encased and hermetically sealed in a housing suitable for implanting in a human body as is known in the art. Power to the PIMD is supplied by an electrochemical power source 520 housed within the PIMD. In one configuration, the power source 520 includes a rechargeable battery. According to this configuration, charging circuitry is coupled to the power source 520 to facilitate repeated non-invasive charging of the power source 520. The communications circuitry 518, or separate receiver circuitry, is configured to receive RF energy transmitted by an external RF energy transmitter. The PIMD may, in addition to a rechargeable power source, include a non-rechargeable battery. It is understood that a rechargeable power source need not be used, in which case a long-life non-rechargeable battery is employed.

The components, functionality, and structural configurations depicted herein are intended to provide an understanding of various features and combination of features that may be incorporated in a PIMD. It is understood that a wide variety of PIMDs and other implantable cardiac monitoring and/or stimulation device configurations are contemplated, ranging from relatively sophisticated to relatively simple designs. As such, particular PIMD or cardiac monitoring and/or stimulation device configurations may include particular features as described herein, while other such device configurations may exclude particular features described herein.

In accordance with embodiments of the invention, a PIMD may be implemented to include an electrode system that provides for one or both of cardiac sensing and arrhythmia therapy delivery. According to one approach, a PIMD may be implemented as a chronically implantable system that performs monitoring, diagnostic and/or therapeutic functions. The PIMD may automatically detect and treat cardiac arrhythmias. In one configuration, the PIMD includes a pulse generator and three or more electrodes that are implanted subcutaneously in the chest region of the body, such as in the anterior thoracic region of the body. The PIMD may be used to provide atrial and ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned U.S. patent application Ser. No. 10/377,274, now U.S. Pat. No. 7,392,081, which is incorporated herein by reference in its entirety.

The PIMD may detect a variety of physiological signals that may be used in connection with various diagnostic, therapeutic or monitoring implementations. For example, the PIMD may include sensors or circuitry for detecting respiratory system signals, cardiac system signals, and signals related to patient activity. In one embodiment, the PIMD senses intrathoracic impedance, from which various respiratory parameters may be derived, including, for example, respiratory tidal volume and minute ventilation. Sensors and associated circuitry may be incorporated in connection with a PIMD for detecting one or more body movement or body posture or position related signals. For example, accelerometers and GPS devices may be employed to detect patient activity, patient location, body orientation, or torso position.

Figure 7:
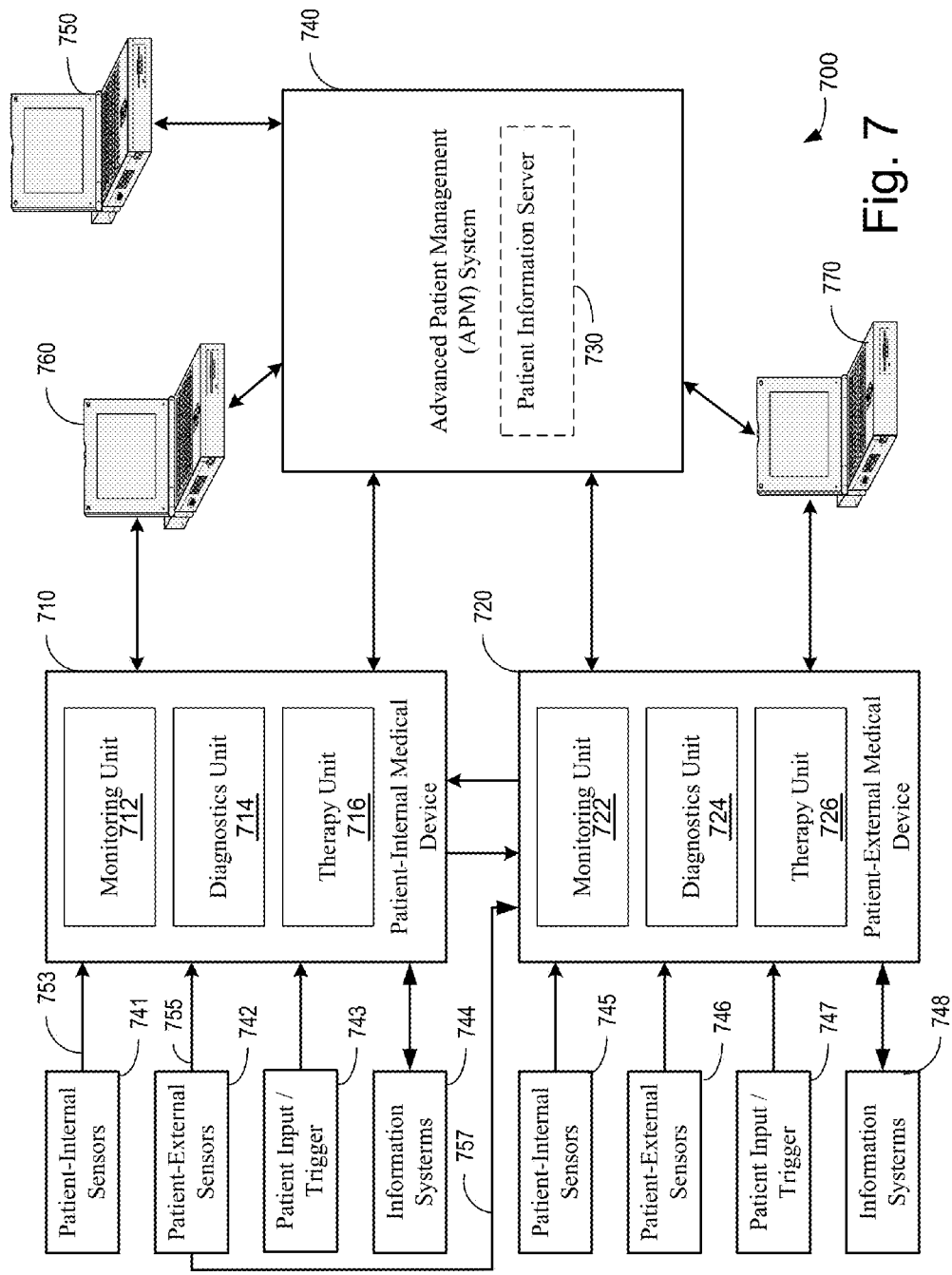
FIG. 7 is a block diagram of a medical system that may be used to implement system updating, coordinated patient monitoring, diagnosis, and/or therapy in accordance with embodiments of the present invention.

Referring now to FIG. 7, a PIMD of the present invention may be used within the structure of an advanced patient management (APM) system 700. The advanced patient management system 700 allows physicians to remotely and automatically monitor cardiac and respiratory functions, as well as other patient conditions. In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 7, the medical system 700 may be used to implement coordinated patient measuring and/or monitoring, diagnosis, and/or therapy in accordance with embodiments of the invention. The medical system 700 may include, for example, one or more patient-internal medical devices 710, such as a PIMD, and one or more patient-external medical devices 720, such as a monitor or signal display device. Each of the patient-internal 710 and patient-external 720 medical devices may include one or more of a patient monitoring unit 712, 722, a diagnostics unit 714, 724, and/or a therapy unit 716, 726.

The patient-external medical device 720 performs monitoring, and/or diagnosis and/or therapy functions external to the patient (i.e., not invasively implanted within the patient's body). The patient-external medical device 720 may be positioned on the patient, near the patient, or in any location external to the patient.

The patient-internal and patient-external medical devices 710, 720 may be coupled to one or more sensors 741, 742, 745, 746, patient input/trigger devices 743, 747 and/or other information acquisition devices 744, 748. The sensors 741, 742, 745, 746, patient input/trigger devices 743, 747, and/or other information acquisition devices 744, 748 may be employed to detect conditions relevant to the monitoring, diagnostic, and/or therapeutic functions of the patient-internal and patient-external medical devices 710, 720.

The medical devices 710, 720 may each be coupled to one or more patient-internal sensors 741, 745 that are fully or partially implantable within the patient. The medical devices 710, 720 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 741 may be coupled to the patient-internal medical device 710 through one or more internal leads 753. Still referring to FIG. 7, one or more patient-internal sensors 741 may be equipped with transceiver circuitry to support wireless communications between the one or more patient-internal sensors 741 and the patient-internal medical device 710 and/or the patient-external medical device 720.

The patient-external sensors 742 may be coupled to the patient-internal medical device 710 and/or the patient-external medical device 720 through one or more internal leads 755 or through wireless connections. Patient-external sensors 742 may communicate with the patient-internal medical device 710 wirelessly. Patient-external sensors 742 may be coupled to the patient-external medical device 720 through one or more internal leads 757 or through a wireless link.

In an embodiment of the present invention, the patient-external medical device 720 includes a visual display configured to concurrently display non-electrophysiological signals and ECG signals. For example, the display may present the information visually. The patient-external medical device 720 may also, or alternately, provide signals to other components of the medical system 700 for presentation to a clinician, whether local to the patient or remote to the patient.

Referring still to FIG. 7, the medical devices 710, 720 may be connected to one or more information acquisition devices 744, 748, such as a database that stores information useful in connection with the monitoring, diagnostic, or therapy functions of the medical devices 710, 720. For example, one or more of the medical devices 710, 720 may be coupled through a network to a patient information server 730.

The input/trigger devices 743, 747 are used to allow the physician, clinician, and/or patient to manually trigger and/or transfer information to the medical devices 710, 720. The input/trigger devices 743, 747 may be particularly useful for inputting information concerning patient perceptions, such as a perceived cardiac event, how well the patient feels, and other information not automatically sensed or detected by the medical devices 710, 720. For example, the patient may trigger the input/trigger device 743 upon perceiving a cardiac event. The trigger may then initiate the recording of cardiac signals and/or other sensor signals in the patient-internal device 710. Later, a clinician may trigger the input/trigger device 747, initiating the transfer of the recorded cardiac and/or other signals from the patient-internal device 710 to the patient-external device 720 for display and diagnosis. The input/trigger device 747 may also be used by the patient, clinician, and/or physician as an activation stimulus to the PIMD to update and/or select a vector.

In one embodiment, the patient-internal medical device 710 and the patient-external medical device 720 may communicate through a wireless link between the medical devices 710, 720. For example, the patient-internal and patient-external devices 710, 720 may be coupled through a short-range radio link, such as Bluetooth, IEEE 802.11, and/or a proprietary wireless protocol. The communications link may facilitate uni-directional or bi-directional communication between the patient-internal 710 and patient-external 720 medical devices. Data and/or control signals may be transmitted between the patient-internal 710 and patient-external 720 medical devices to coordinate the functions of the medical devices 710, 720.

In another embodiment, patient data may be downloaded from one or more of the medical devices periodically or on command, and stored at the patient information server 730. The physician and/or the patient may communicate with the medical devices and the patient information server 730, for example, to acquire patient data or to initiate, terminate or modify recording and/or therapy.

The data stored on the patient information server 730 may be accessible by the patient and the patient's physician through one or more terminals 750, e.g., remote computers located in the patient's home or the physician's office. The patient information server 730 may be used to communicate to one or more of the patient-internal and patient-external medical devices 710, 720 to provide remote control of the monitoring, diagnosis, and/or therapy functions of the medical devices 710, 720.

In one embodiment, the patient's physician may access patient data transmitted from the medical devices 710, 720 to the patient information server 730. After evaluation of the patient data, the patient's physician may communicate with one or more of the patient-internal or patient-external devices 710, 720 through an APM system 740 to initiate, terminate, or modify the monitoring, diagnostic, and/or therapy functions of the patient-internal and/or patient-external medical systems 710, 720.

In another embodiment, the patient-internal and patient-external medical devices 710, 720 may not communicate directly, but may communicate indirectly through the APM system 740. In this embodiment, the APM system 740 may operate as an intermediary between two or more of the medical devices 710, 720. For example, data and/or control information may be transferred from one of the medical devices 710, 720 to the APM system 740. The APM system 740 may transfer the data and/or control information to another of the medical devices 710, 720.

In one embodiment, the APM system 740 may communicate directly with the patient-internal and/or patient-external medical devices 710, 720. In another embodiment, the APM system 740 may communicate with the patient-internal and/or patient-external medical devices 710, 720 through medical device programmers 760, 770 respectively associated with each medical device 710, 720. As was stated previously, the patient-internal medical device 710 may take the form of an implantable PIMD.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable cardiac device, comprising:
   a housing configured for implantation in a patient;
   an implantable sensor configured to sense transthoracic impedance;
   an implantable activity sensor configured to make an activity measurement indicative of patient activity;
   a memory provided in the housing;
   a controller provided in the housing and operatively coupled to the respective sensors and the memory, the controller configured to:
   determine a patient index based at least part on the sensed transthoracic impedance;
   detect a physiological condition based on the determined patient index being beyond a threshold, the threshold based at least in part on a plurality of previous patient index values and associated patient activity levels; and
   provide an output based, at least in part, on the detected physiological condition.

2. The device according to claim 1, wherein the controller is configured to determine the patient index based at least in part on a ratio of a respiratory rate value and a tidal volume value for the patient.

3. The device according to claim 1, wherein the threshold is based on a profile developed by the controller using a plurality of previous patient index values and associated patient activity levels acquired over time.

4. The device according to claim 1, wherein the controller is configured to trend a plurality of patient index values to determine at least part of a patient profile, wherein the threshold is based at least in part on the patient profile.

5. The device according to claim 1, wherein the controller is configured to trend a plurality of patient index values and their associated patient activity levels to develop a patient index versus activity level profile, and wherein the threshold is based at least in part on the patient index versus activity level profile.

6. The device according to claim 5, wherein the controller is configured to detect the physiological condition using the threshold that is based at least in part on the patient index versus activity level profile.

7. The device according to claim 1, wherein the physiological condition relates to congestive heart failure (CHF).

8. The device according to claim 7, wherein the output relates to monitoring, diagnosis and/or therapy of congestive heart failure (CHF).

9. The device according to claim 1, comprising:
an implantable electrode arrangement; and
therapy circuitry provided in the housing and coupled to the controller and the implantable electrode arrangement, the therapy circuitry configured to deliver a therapy via the electrode arrangement based at least in part on the patient index and the associated patient activity.

10. The device according to claim 1, comprising:
an implantable electrode arrangement; and
therapy circuitry provided in the housing and coupled to the controller and the implantable electrode arrangement, the therapy circuitry configured to deliver a cardiac therapy via the electrode arrangement that changes a pacing rate by a predetermined amount when the physiological condition is detected.

11. The device according to claim 1, wherein:
the controller is configured to generate an alert in response to the patient index being beyond the threshold and a trend of the patient index indicative of worsening of congestive heart failure (CHF); and
the controller cooperates with communication circuitry to transmit the alert to an external device.

12. A system, comprising:
a sensor configured to sense transthoracic impedance;
an activity sensor configured to sense a patient activity level;
a memory;
a controller operatively coupled to the respective sensors and the memory, the controller configured to:
repeatedly determine a patient index value based at least in part on the sensed transthoracic impedance, and associate each of the patient index values with a corresponding activity level value detected at least in part by the activity sensor;
determine a patient index versus activity level profile based at least in part on one or more of the patient index values and corresponding activity level values; and
provide an output based, at least in part, on the patient index versus activity level profile.

13. The system of claim 12, wherein the patient index versus activity level profile includes a plurality of patient index values associated with different ranges of patient activity levels.

14. The system of claim 12, wherein the controller is configured to repeatedly determine a respiration rate (RR) and tidal volume (TV) of the patient based at least in part on the sensed transthoracic impedance and determine the patient index values based at least in part on the respiration rate (RR) and tidal volume (TV).

15. The system of claim 12 wherein the patient index values and the corresponding activity level values are stored in the memory.

16. The system of claim 12, wherein the controller trends the patient index values.

17. The system of claim 12, wherein the output adapts a therapy provided by the cardiac device.

18. The system of claim 17, wherein the output relates to monitoring, diagnosis and/or therapy of a congestive heart failure (CHF) therapy condition.

19. A system, comprising:
a sensor configured to sense transthoracic impedance;
an activity sensor configured to make an activity measurement indicative of patient activity;
a memory configured to store at least a patient index versus activity level profile that is based on a plurality of patient index values associated with different ranges of patient activity levels;
a controller operatively coupled to the respective sensors and the memory, the controller configured to:
determine a plurality of patient index values over time, each of the plurality of patient index values based at least part on the sensed transthoracic impedance;
determine a plurality of patient activity levels over time, wherein the plurality of patient activity levels are based at least in part on the activity sensor;
detect a physiological condition based on one or more patient index values exceeding a threshold of the patient index versus activity level profile, the threshold being associated with an activity range of the profile that the patient activity level is determined to be within; and
provide an output based, at least in part, on the detected physiological condition.

20. The system according to claim 19, wherein the controller is configured to determine the plurality of patient index values based at least in part on a ratio of a respiratory rate value and a tidal volume value for the patient.

* * * * *